United States Patent [19]

Makofski et al.

[11] Patent Number: 4,821,729
[45] Date of Patent: Apr. 18, 1989

[54] MEANS AND METHOD FOR THE NONINVASIVE FRAGMENTATION OF BODY CONCRETIONS HAVING MEANS FOR ACCURATELY LOCATING A CONCRETION

[75] Inventors: Robert A. Makofski, Catonsville; Joe T. Massey, Bethesda; F. Fausten Mark, Silver Spring; Francis B. Weiskopf, Jr., Catonsville; William H. Guier, Pasadena; Patrick C. Walsh, Hunt Valley; Fray F. Marshall, Ruxton, all of Md.

[73] Assignee: The Johns Hopkins University, Baltimore, Md.

[21] Appl. No.: 905,218

[22] Filed: Sep. 9, 1986

Related U.S. Application Data

[63] Continuation-in-part of Ser. No. 608,114, May 8, 1984, Pat. No. 4,610,249.

[51] Int. Cl.⁴ ............................................. A61B 17/22
[52] U.S. Cl. .............................. 128/660.03; 128/24 A; 128/328
[58] Field of Search ...................... 128/660, 328, 24 A, 128/804

[56] References Cited

U.S. PATENT DOCUMENTS

| | | | |
|---|---|---|---|
| 4,526,168 | 7/1985 | Hassler et al. | 128/328 |
| 4,620,546 | 11/1986 | Aida et al. | 128/660 |
| 4,669,483 | 6/1987 | Hepp et al. | 128/660 |

*Primary Examiner*—Ruth S. Smith
*Attorney, Agent, or Firm*—Robert E. Archibald; Francis A. Cooch

[57] ABSTRACT

Apparatus and method for noninvasive fragmentation of body concretions. The apparatus has an integral unit including an ultrasonic locating transducer a relative position determining device, a shockwave generating device and a positioning structure. The method for locating a body concretion includes the steps of locating the body concretion with ultrasonics, the position of the shockwave generating device relative to the concretion, accurately positioning the shockwave generating device at the location of the concretion and then shattering the concretion by generating a shockwave. The shockwave generating device includes a reflector with first and second foci, a location verifying ultrasonic transducer which is positioned so that an axis of the verifying transducer is coincident with a straight line passing through the first and second foci and a spark gap at the first focus which generates the shockwave.

4 Claims, 3 Drawing Sheets

4,821,729

MEANS AND METHOD FOR THE NONINVASIVE FRAGMENTATION OF BODY CONCRETIONS HAVING MEANS FOR ACCURATELY LOCATING A CONCRETION

REFERENCE TO RELATED APPLICATION

This application is a continuation-in-part of application Ser. No. 608,114, filed May 8, 1984, now U.S. Pat. No. 4,610,249 entitled "Means and Method for Noninvasive Fragmentation of Body Concretions".

BACKGROUND OF THE INVENTION

This invention relates generally to a device for the noninvasive fragmentation of body concretions and more particularly to a device with an integral ultrasonic locating and positioning means whereby the concretion is localized with ultrasonics and the device is positioned in response to ultrasonicly derived information.

The formation of body concretions is a fairly common occurrence in humans. For example, it is estimated that one of every ten American males and one of every forty American females will be treated for kidney stones, one of the most common body concretions, during their lifetime. The occurrence of kidney stones is usually debilitating to the patient and causes a significant loss of productive labor to industry. In many cases, treatment requires major and often repeated surgery. Many attempts have been made to develop a simple and effective noninvasive treatment of kidney stones. One such method involves chemical dissolution of the stone, however, most of these attempts have been unsuccessful and impractical because of the slowness of the dissolution process.

Another method involves the direct contact of the concretion by the energy source. As such the procedures of this method are either transurethral or surgical. Two of the most common procedures are the electrohydraulic shockwave and the ultrasonic lithotripter. The electrohydraulic shockwave is generated via two well-isolated, high voltage leads which are carried by a common cystoscope to the stone and a high capacity condenser is discharged via the probe causing a spark to jump between two poles. This sparking causes a hydrodynamic wave which destroys the concretion upon contact. The ultrasonic lithotripter device produces ultrasonic waves which are carried by a hollow steel probe to the concretion. These two methods are generally limited to treatment of bladder stones.

The advent of high-speed physics and the development of a method of generating shockwaves by an underwater spark gap led to a method of noninvasive fragmentation of body concretions. One such device for the noninvasive fragmentation of kidney stones includes a large bath in which the patient is immersed, crossed X-ray beams for the localization of the stone and an underwater spark gap for the generation of high energy shockwaves which are focused at the kidney stone.

As can be appreciated a system such as described above has many disadvantages. The large space required for the bath and the X-ray system as well as the electronics for the generation of the underwater spark gap is a major detriment. Another detriment is that it reuires multiple shockwaves to fragment the stone to particles that will pass through the urinary system and the repeated positioning of the spark gap apparatus required multiple X-rays which are very detrimental to the patient.

It is therefore one object of this invention to provide a method and apparatus for the noninvasive fragmentation of body concretions that is simple, small in size, effective and inexpensive for the patient.

It is another object of this invention to provide a method and apparatus for the noninvasive fragmentation of body concretions that does not require multiple X-rays of the patient.

It is a further object of this invention to provide method and apparatus for the noninvasive fragmentation of body concretions that does not require the immersion of the patient.

Other objects, advantages and novel features of the present invention will become apparent from the following detailed description of the invention when considered in conjunction with the accompanying drawings.

SUMMARY OF THE INVENTION

These and other objects, features and advantages of the invention are accomplished by an integrated ultrasonic system, relative position system and shockwave generating system wherein the ultrasonic system localizes the concretion and the relative position system determines the relative position of the shockwave generating system relative to the concretion so that the shockwave generating system can be accurately positioned at the concretion. The shockwave generating system utilizes a reflector with a first and second focus with a spark gap located at the first focus and the reflector accurately positioned so that the body concretion is located at the second focus. A flexible membrane encloses the fluid filled reflector and provides an interface between the patient and shockwave generator for the efficient transmission of the shockwave energy to the body concretion.

BRIEF DESCRIPTION OF THE DRAWINGS

The above and further objects and novel features of the invention will more fully appear from the following description when the same is read in connection with the accompanying drawings. It is to be understood, however, that the drawings are for the purpose of illustration only, and are not intended as a definition of the limits of the invention.

DESCRIPTION OF THE PREFERRED EMBODIMENT

Figure 1:
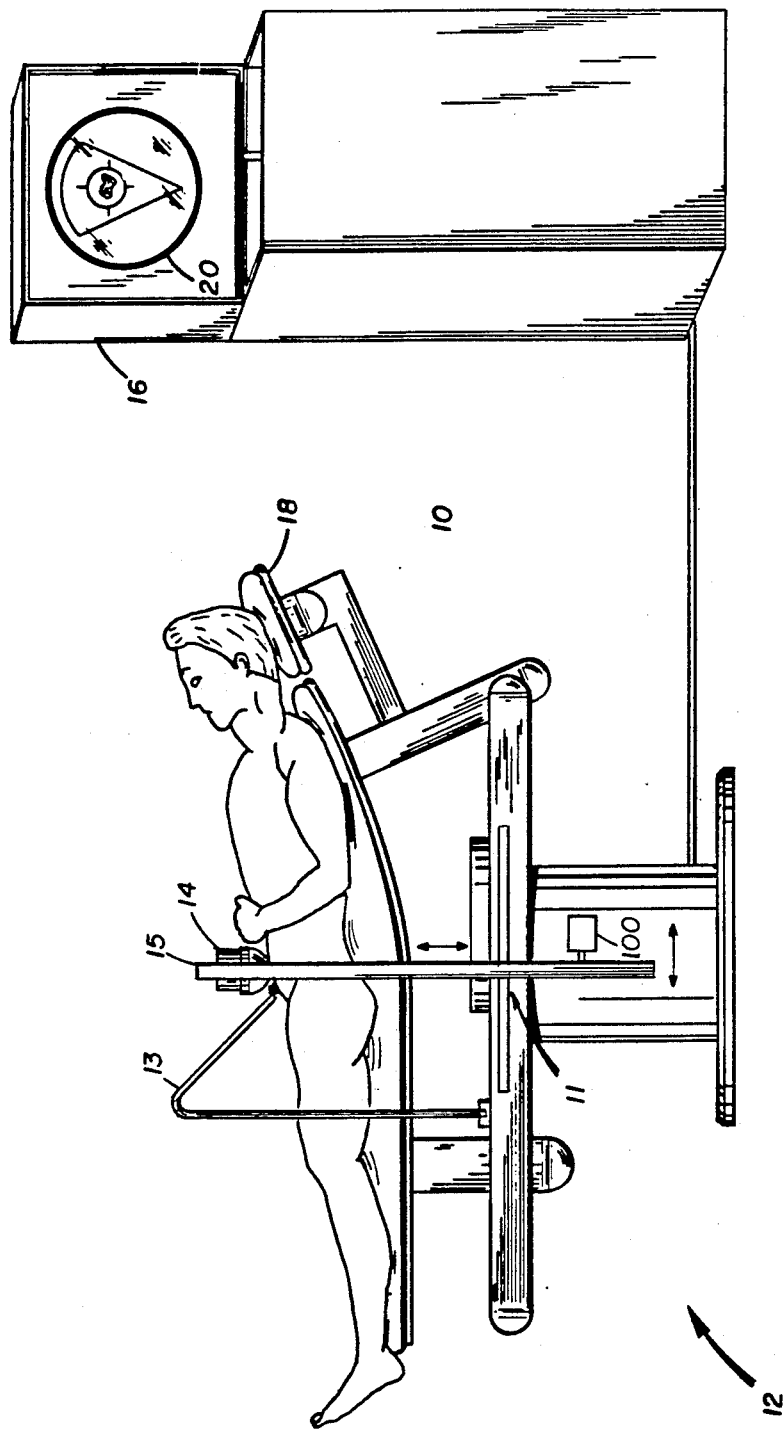
FIG. 1 is a pictorial representation of the present invention.

Referring now to the drawings, FIG. 1 is a pictorial representation of the system 10 as taught by the present invention. The system comprises four main sections; (1) the patient support system 12, (2) the shockwave/ultrasonic section 14, (3) the ultrasonic display and control section 16 and (4) the first ultrasonic section 13. The patient support system 12 shown in the drawing is a table 18. The shockwave/ultrasonic section 14 is mounted on an arc 15. The arc 15 is attached to the table 18 by universal connections at 11 which permits movement of the arc 15 across the body of a patient and parallel to the body of the patient. The shockwave/ultrasonic section 14 in combination with arc 15 can also be moved perpendicular to the body of the patient.

The first ultrasonic transducer section 13 is flexibly mounted to the table to permit movement in three orthogonal axes. The system 10 also includes a relative position device for determining the relative location of a body concretion, which is located by the first ultrasonic section 13, to that of the shockwave/ultrasonic section 14. The relative position device will be described in greater detail below. The first ultrasonic section includes a first ultrasonic transducer, to be described below, which provides ultrasonic location information of the concretion to the ultrasonic display and control section 16.

The shockwave/ultrasonic section 14 includes a second ultrasonic transducer, to be described below, which provides ultrasonic location information of the concretion to ultrasonic display and control section 16. The ultrasonic display and control section 16 selectively displays the location information of the first and second ultrasonic transducer on a visual display 20. A doctor or technician utilizes the location information from the first transducer to locate the concretion. Location information from the second transducer is used to verify that the shockwave/ultrasonic section 14 is in a position at the location of the concretion in which the shockwave will be most effective in fragmenting the concretion.

The method for using system 10 is as follows: The technician, first moves the first ultrasonic transducer about the patient's body until the concretion is located. Once the concretion is located, the relative position device is activated to determine the relative position of the shockwave/ultrasonic section 14 to the concretion. The relative position device outputs a relative position signal indicative of the relative position of the shockwave ultrasonic section 14 to the first ultrasonic transducer. The relative position signal is used to either manually or automatically move the shockwave/ultrasonic section to the location of the concretion as verified by the second ultrasonic transducer. When the shockwave/ultrasonic section 14 is positioned correctly as indicated by location information from the second transducer the technician causes a shockwave to be generated from the shockwave/ultrasonic section 14.

Figure 2:
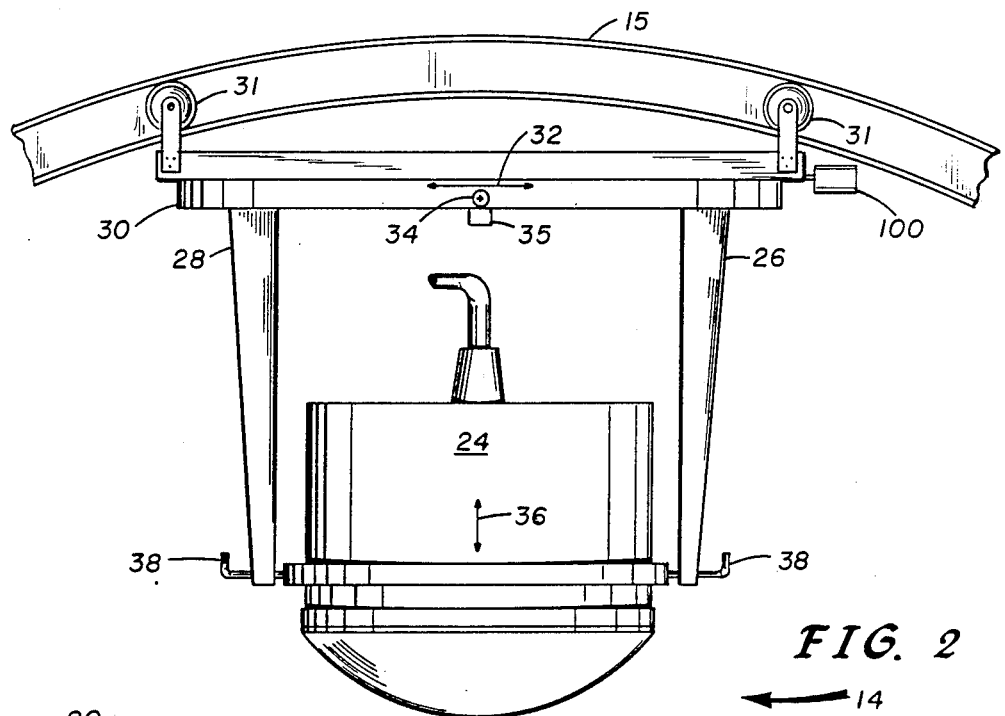
FIG. 2 is a pictorial representation of the shockwave-ultrasonic section and a section element of the relative position system.

FIG. 2 is a pictorial representation of the shockwave/ultrasonic section 14 mounted on the arc 15. The shockwave/ultrasonic section 14 comprises a main housing 24, a second element 35 of the relative position device and a support structure comprising legs 26, 28 mounted on a movable member 30 which is mounted on member 31. Member 31 may be wheels or some other device mounted on arc 15 which permit movement of the shockwave/ultrasonic section 14 about arc 15. Member 30 is movable in a first direction represented by arrow 32 and in a second direction represented by the tail of arrow 34 shown going into the plane of the drawing. The main housing 24 is movable in a third direction represented by arrow 36. Movement in any of the directions may be remotely controlled in which case motors mounted in shockwave/ultrasonic section 14 and in universal connection 11 would move the main housing 24 in response to the relative position signal 24. Alternatively, it is contemplated that movement in each or all three of the directions may be accomplished manually in which case handles, such as those shown at 38 could be loosened to allow the main housing 24 to be moved in the third direction, represented at 36, along tracks, not shown, the legs 26, 28, until the correct position is reached whereupon handles 38 are tightened to maintain the main housing 24 in position.

Figure 3:
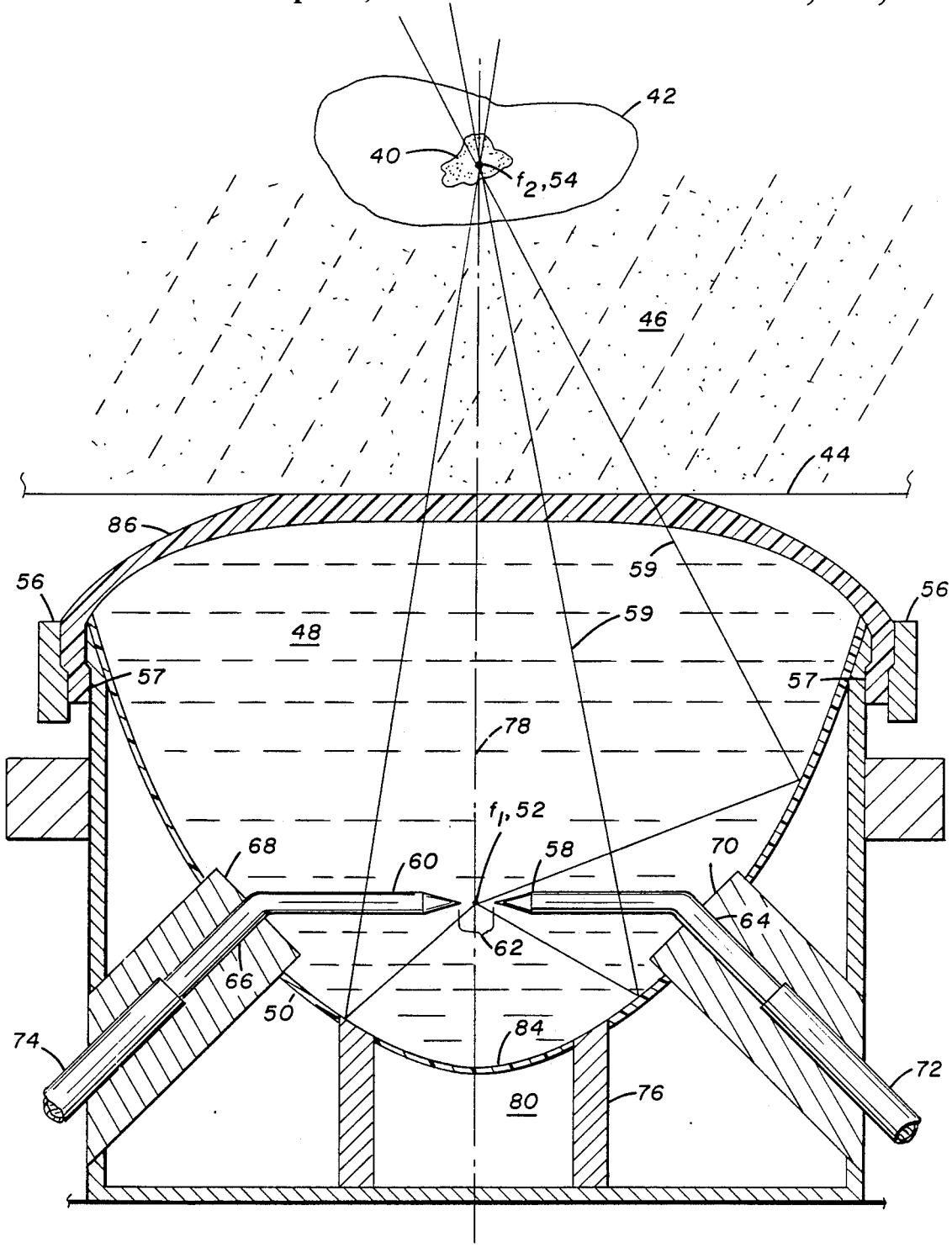
FIG. 3 is a cross sectional view of the main housing which includes the reflector and transducer.

FIG. 3 is a cross sectional view of main housing 24 and shows the positioning of the main housing 24 in relation to a concretion such as a kidney stone, represented at 40, in a human kidney, represented at 42. The patient's skin is represented at 44 and a portion of body tissue is represented at 46. The main housing 24 comprises a closed space 48 filled with a fluid with acoustical properties essentially similar to the acoustical properties of body tissue. Such a fluid could be water or a saline solution of water.

One portion of enclosed space 48 is bounded by a reflector surface 50 with a first focus $f_1$, represented at 52 and a second focus, $f_2$, represented at 54. The reflector surface of the preferred embodiment is described by an ellipsoid of revolution. The remaining portion of enclosed space 48 is bounded by a flexible membrane 86 which is held in place by a clamping ring 56 against an outer surface 57 of main housing 24. Electrodes 58, 60 with a spark gap, indicated at 62, centered around the first focus, $f_1$, 52 are throughput housing 24 at 64, 66 with suitable means for insulation 68, 70 from the structure of main housing 24. Leads 72, 74 lead to a high voltage supply, not shown. The spark gap 62 in the preferred embodiment is approximately 2–4 mm and the high voltage power supply provides a voltage across electrodes 58, 60 of approximately 10,000 volts. The generation of a spark between electrodes 58, 60 at the first focus $f_1$ causes a shockwave which is focused by the reflector surface 50 at the second focus $f_2$. Rays 59 indicate the focusing of the shockwave. The spark gap shown in FIG. 3 can be replaced with a laser to generate the shockwave.

The second ultrasonic transducer 76 being used to verify the location of the concretion and to correctly position the shockwave/ultrasonic section 14 at the location of the concretion is made integral with main housing 24 and is positioned at an end of the reflector surface 50. The second ultrasonic transducer 76 is positioned so that an axis of the transducer is coincident with a line, indicated at 78, extending through the first and second focus, $f_1$ and $f_2$, of the ellipsoid of revolution. The second transducer 76 is rotatable around the line 78 for at least an angle of $\pm 90$ degrees. The second transducer 76 includes a radiating and detecting element 80 which radiates an acoustical signal and detects reflected portions of the acoustical signal. A flexible membrane 84 provide an interface between the radiating and detecting element 80 and the space 48.

Figure 5:
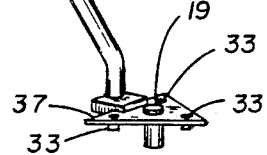
FIG. 5 is a pictorial representation of the flexible arm, first transducer and a first element of the relative position system.
Figure 6:
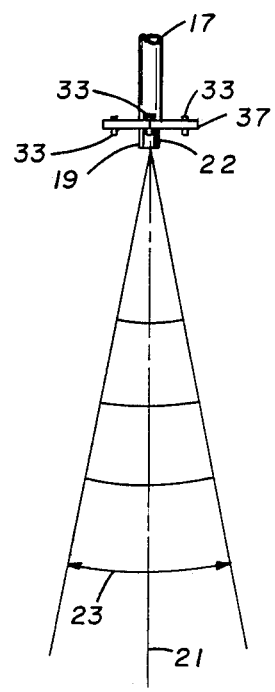
FIG. 6 is a cross sectional view of the first transducer and the first relative element and a graphical representation of the radiated ultrasonic energy.

The first ultrasonic section 13 shown in FIGS. 5 and 6 includes a flexible arm 17, a first element 37 of the relative position device and a first ultrasonic transducer 19. One end of the flexible arm 17 is stationarily attached to the table 18 with the other end being attached to the first transducer 19. The first ultrasonic transducer 19, through use of the flexible arm, can be manipulated in three orthogonal axes by the technician to locate the concretion. The first transducer 19 is rotatable around a line 21 for at least an angle of ±90 degrees. The first transducer 19 includes a radiating and detecting element 22 which radiates an acoustical signal and detects reflected portions of the acoustical signal. FIG. 6 provides a pictorial representation of the first transducer 19 and a graphical representation of the radiated ultrasonic radiation. The radiated acoustical signal is traversed in a plane within an angle 23 centered on line 21. As can be appreciated, a rotation of transducer 19 causes a rotation of the plane in which the acoustical signal traverses. The transducer 19 is caused to be manipulated in three orthogonal axes and rotated by the doctor or technician until a body concretion is indicated on visual display 20.

The relative position device includes a second element 35 shown in FIG. 2, a first element 37 shown in FIGS. 5 and 6 and a processing circuit included in the control section 16. The second element 35 of the relative position device is a microphone. The first element 37 of the relative position device includes a plate and a plurality of spark dischargers 33. Each spark discharger 33 creates a short burst of acoustical noise upon initiation. As shown in FIG. 6, the spark dischargers 33 are placed symmetrically about the axis of the first transducer 19.

The relative position device determines the relative position of the shockwave/ultrasonic section 14 to the concretion located by the first transducer 19. The relative position is determined by initiating operation of the spark dischargers 33. Each spark discharger generates a short burst of acoustical noise. By generally known in the art timing circuits the spark dischargers are squentially timed so that sequential bursts are produced. The second element 35 of the relative position system, the microphone, detects the sequential bursts and provides a signal, indicative thereof, to the processing circuit of the relative position device. The processing circuit determines the relative position by using the time elapsed from initiation to receipt of the sequential bursts and the timing between each burst. The processing circuit provides a relative position signal indicative of the relative position of the shockwave/ultrasonic section 14. The relative position signal is thereafter used to position the shockwave/ultrasonic section 14 to the location of the concretion.

Figure 4:
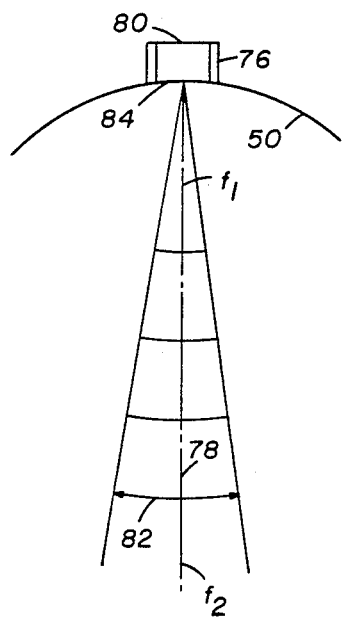
FIG. 4 is a pictorial representation of a portion of the main housing and a graphical representation of the radiated ultrasonic energy.

FIG. 4 is a pictorial representation of main housing 24 and transducer 76 and a graphical representation of the radiated ultrasonic radiation. The radiated acoustical signal is traversed in a plane within an angle 82 centered on line 78. As can be appreciated, a rotation of transducer 76 causes a rotation of the plane in which the acoustical signal traverses. The detected reflected acoustical signal is displayed on visual display 20 on display and control section 16 (FIG. 1). The transducer 76 is caused to rotate by the doctor or technician until a body concretion is indicated on visual display 20. The doctor or technician automatically or manually moves the main housing in the first, second and third direction as in response to the relative location signal discussed above until the concretion is located at the second focus of reflector 50. The third direction is perpendicular to both the first and second directions and is essentially perpendicular to the patient's body, i.e., movement in the third direction moves the main housing closer to or further away from the patient's body. Once the concretion is visually indicated as being at the second focal point $f_2$, a shockwave is initiated by the doctor and the process is repeated until the concretion is fragmented.

While the invention has been described with reference to the accompanying drawings, it is to be clearly understood that the invention is not to be limited to the particular details shown therein as obvious modifications may be made by those skilled in the art. The embodiments should only be construed within the scope of the following claims.

What is claimed is:

1. A device for the noninvasive fragmentation of a concretion within a body of a patient, comprising:
   patient support means;
   a first ultrasonic transducer mounted on said patient support means, said first ultrasonic transducer being used to locate said concretion;
   a second ultrasonic trnsducer for locating said concretion;
   a reflector comprising a portion of an ellipsoid of revolution with an open end and a closed end, said second ultrasonic transducer being attached to said closed end, said reflector having a first focus and a second focus, said second ultrasonic transducer being positioned so that an axis of the second ultrasonic transducer is coincident with the straight line extending through the first and second foci;
   relative positioning means for determining the relative position of said reflector to the location of said concretion as determined by said first ultrasonic transducer and providing a relative position signal indicative of the relative position of said reflector;
   reflector positioning means for positioning said reflector at the location of said concretion in response to said relative position signal from said relative positioning means and wherein said concretion is located at the second focus of said reflector using said second ultrasonic transducer; shockwave generating means for generating a shockwave at said first focus; and
   acoustical coupling means for acoustically coupling said shockwave from said first focus through a portion of said body to said second focus whereby said shockwave is concentrated at said concretion.

2. A device as recited in claim 1, wherein said relative positioning means comprises:
   acoustical noise means having a plurality of spark dischargers symmetrically disposed about said first ultrasonic transducer for generating sequential bursts of acoustical noises;
   acoustical noise detecting means for detecting the sequential bursts of noises and providing a signal indicative of said sequential bursts of acoustical noises; and
   relative position circuit means for processing the signal from said acoustical noise detecting means and providing a relative position signal indicative of the relative position of said reflector.

3. A method for the noninvasive fragmentation of a concretion within a body of a patient, comprising the steps of:
   providing a patient support means;
   providing a first ultrasonic transducer mounted on said patient support means;
   providing a reflector comprising a portion of an ellipsoid of revolution with an open end and closed end having first and second foci and a second ultrasonic transducer having an axis coincident with a straight line passing through said first and second foci, said second ultrasonic transducer attached to the closed end of said reflector;
ultrasonically locating the concretion with said first ultrasonic transducer;
determining the relative position of said reflector to said concretion and providing a relative position signal indicative of said relative position;
positioning said reflector at the location of said concretion in response to said relative position signal;
verifying the location of said concretion with said second ultrasonic transducer whereby said concretion is located at the second focus of said reflector;
generating a shockwave at the first focus; and
acoustically coupling the shockwave from the first focus through a portion of the body to the second focus whereby the shockwave is concentrated at the concretion.

4. A method as recited in claim 3, wherein said step of determining the relative position of said reflector to said concretion further comprising the steps of:
generating sequential bursts of acoustical noises from a plurality of spark discharges disposed symmetrically about said first ultrasonic transducer;
detecting said sequential bursts of acoustical noises and providing a signal indicative of said sequential bursts of acoustical noise; and
processing said signal indicative of said sequential bursts of acoustical noises and providing a relative position signal indicative of the relative position of said reflector.

* * * * *